US009932977B2

(12) United States Patent
Bresina et al.

(10) Patent No.: US 9,932,977 B2
(45) Date of Patent: Apr. 3, 2018

(54) INFUSION SYSTEM DISPOSABLE ALIGNMENT SYSTEM

(71) Applicant: Smiths Medical ASD, Inc., Rockland, MA (US)

(72) Inventors: Timothy B. Bresina, Shoreview, MN (US); Renee Robert, Shoreview, MN (US); Grant Adams, Coon Rapids, MN (US)

(73) Assignee: Smiths Medical ASD, Inc., Plymouth, MN (US)

( * ) Notice: Subject to any disclaimer, the term of this patent is extended or adjusted under 35 U.S.C. 154(b) by 267 days.

(21) Appl. No.: 14/433,326

(22) PCT Filed: Oct. 7, 2013

(86) PCT No.: PCT/US2013/063646
§ 371 (c)(1),
(2) Date: Apr. 2, 2015

(87) PCT Pub. No.: WO2014/062403
PCT Pub. Date: Apr. 24, 2014

(65) Prior Publication Data
US 2015/0273140 A1    Oct. 1, 2015

Related U.S. Application Data

(60) Provisional application No. 61/713,906, filed on Oct. 15, 2012.

(51) Int. Cl.
*F04B 43/12* (2006.01)
*F04B 39/14* (2006.01)
(Continued)

(52) U.S. Cl.
CPC ......... *F04B 43/12* (2013.01); *A61M 5/14228* (2013.01); *F04B 17/06* (2013.01);
(Continued)

(58) Field of Classification Search
CPC ........ F04B 43/082; F04B 43/08; F04B 43/12; F04B 45/06; F04B 45/08; F04B 53/16;
(Continued)

(56) References Cited

U.S. PATENT DOCUMENTS 4,565,542 A    1/1986   Berg
4,650,469 A    3/1987   Berg
(Continued)

FOREIGN PATENT DOCUMENTS

WO    WO 02-055137 A2    7/2002

OTHER PUBLICATIONS

International Application No. PCT/US2013/063646, International Search Report, dated Jan. 8, 2014, 4 pages.
(Continued)

*Primary Examiner* — Bryan Lettman
(74) *Attorney, Agent, or Firm* — Patterson Thuente Pedersen

(57) ABSTRACT

A medical infusion pump pressure plate alignment system and components that include a chassis, a sensor module, and a pressure plate in various embodiments. The pressure plate has a first end pivotally mounted to the chassis of the control module for pivotal retention and a second end selectively mounted to the chassis of the control module. The pressure plate, hooks or rail contain recessed or projection features configured for receipt of the complementary features of the sensor module. Additional alignment features can include a retaining component incorporated with the hook, a guide feature on the outer surface of the pressure plate, and a kickstand feature attached to the rail.

8 Claims, 15 Drawing Sheets

(51) Int. Cl.
*F04B 39/12* (2006.01)
*F04B 43/08* (2006.01)
*F04B 17/06* (2006.01)
*A61M 5/142* (2006.01)
*A61M 5/36* (2006.01)

(52) U.S. Cl.
CPC ............ *F04B 39/121* (2013.01); *F04B 39/14* (2013.01); *F04B 43/082* (2013.01); *A61M 5/365* (2013.01); *A61M 2205/12* (2013.01); *A61M 2205/121* (2013.01); *A61M 2205/6045* (2013.01)

(58) Field of Classification Search
CPC ........ F04B 39/12; F04B 39/121; F04B 39/14; F04B 41/02; F04B 23/02; F04B 23/025; F04B 23/026; F04B 17/06; F04B 35/06; F04B 53/22; A61M 1/0259; A61M 1/10–1/1084; A61M 5/142; A61M 5/14228; A61M 5/14232
See application file for complete search history.

(56) References Cited

U.S. PATENT DOCUMENTS

| | | | |
|---|---|---|---|
| 5,009,641 A | 4/1991 | Gorton | |
| 5,458,578 A | 10/1995 | Sebesta | |
| 5,522,799 A | 6/1996 | Furukawa | |
| 5,531,697 A * | 7/1996 | Olsen | A61M 5/142 128/DIG. 12 |
| 5,658,252 A | 8/1997 | Johnson | |
| 5,718,816 A | 2/1998 | Savage | |
| 5,772,409 A | 6/1998 | Johnson | |
| 5,788,671 A | 8/1998 | Faust | |
| 5,823,746 A | 10/1998 | Johnson | |
| 5,928,196 A | 7/1999 | Johnson | |
| 5,954,485 A | 9/1999 | Johnson | |
| 6,077,055 A * | 6/2000 | Vilks | A61M 5/16854 417/44.2 |
| 6,106,498 A | 8/2000 | Friedli | |
| 6,142,446 A | 11/2000 | Leinsing | |
| 6,202,708 B1 * | 3/2001 | Bynum | A61M 5/1409 141/105 |
| 6,231,320 B1 | 5/2001 | Lawless | |
| 6,423,053 B1 | 7/2002 | Lee | |
| 6,902,207 B2 | 6/2005 | Lickliter | |
| 7,967,773 B2 | 6/2011 | Amborn | |
| 8,118,781 B2 | 2/2012 | Knopper | |
| 2002/0159900 A1 | 10/2002 | Lawless | |
| 2004/0227120 A1 | 11/2004 | Raybuck | |
| 2005/0209552 A1 | 9/2005 | Beck | |
| 2006/0173412 A1 | 8/2006 | Susi | |
| 2008/0065016 A1 | 3/2008 | Peters | |
| 2009/0043252 A1 | 2/2009 | Haylor | |
| 2009/0264857 A1 | 10/2009 | Susi | |
| 2012/0082576 A1 * | 4/2012 | Beck | F04B 43/0081 417/474 |

OTHER PUBLICATIONS

Extended European Search Report, Application No. 13847576.9, dated Oct. 19, 2016, 13 pages.
Supplementary European Search Report, Application No. 13847576.9, dated Jun. 23, 2016, 8 pages.
International Preliminary Report on Patentability, Application No. PCT/US2013/063646, report dated Apr. 21, 2015, 9 pages.

* cited by examiner

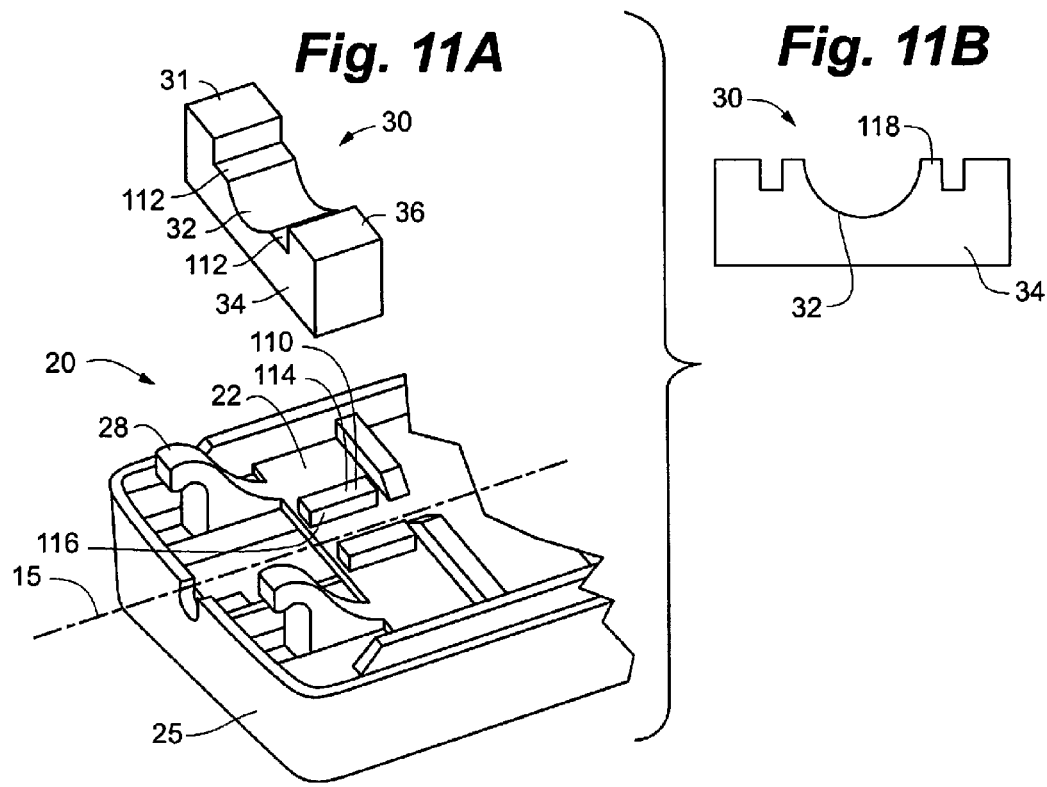
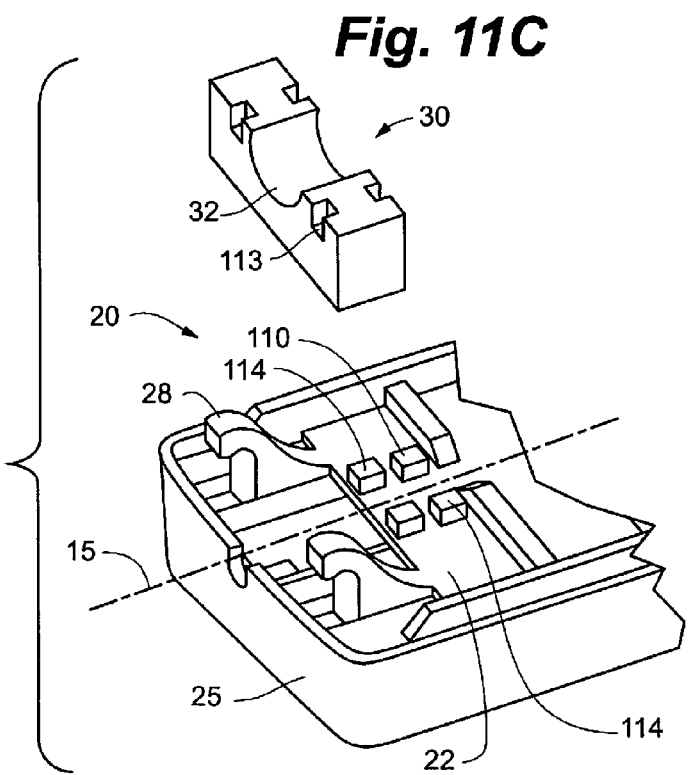

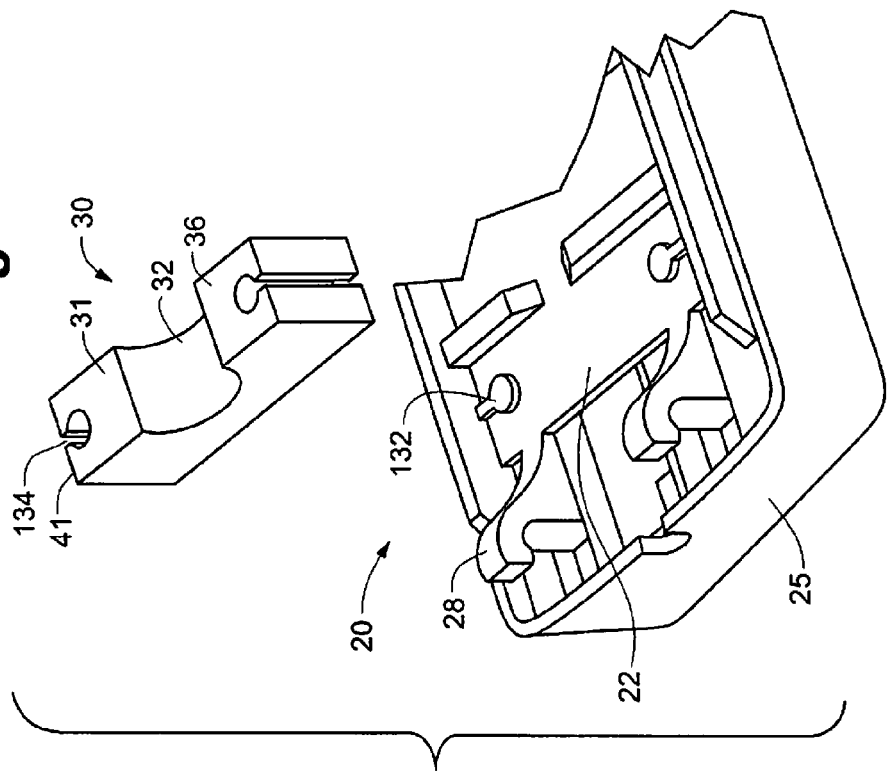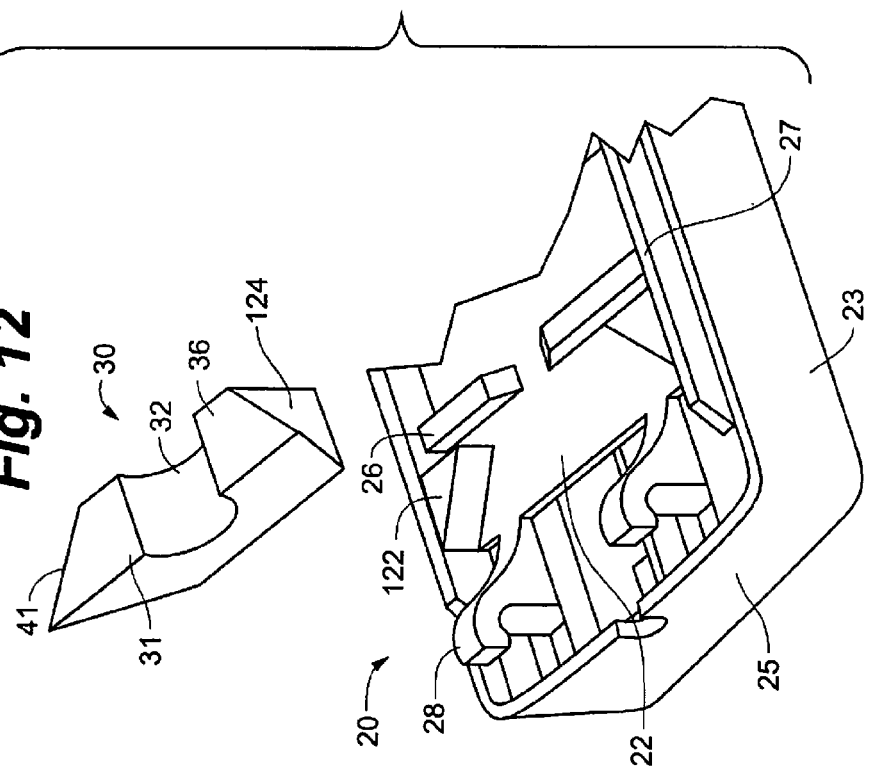

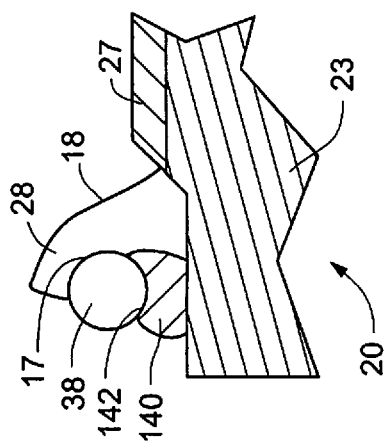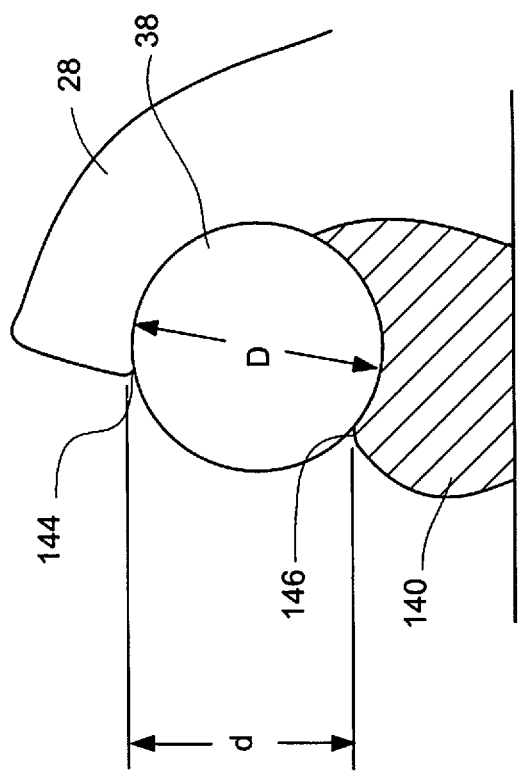

INFUSION SYSTEM DISPOSABLE ALIGNMENT SYSTEM

RELATED APPLICATION

This application is a National Phase entry of PCT Application No. PCT/US2013/063646 filed Oct. 7, 2013, which application claims the benefit of priority of U.S. Provisional Patent Application No. 61/713,906 filed Oct. 15, 2012, the entire disclosures of which are incorporated herein by reference.

TECHNICAL FIELD

Subject matter hereof relates generally to medical infusion systems and more particularly to a pressure plate alignment system for a disposable medication cassette or disposable administration set used with medical infusion pumps and various apparatus and methods thereof.

BACKGROUND

Infusion systems and medication delivery devices, such as infusion pumps, are well known and widely used throughout the world today. Intravenous infusion pumps were developed decades ago to pump medicaments, nutrients or other fluids through tubing to a patient in connection with treatment of a medical condition. Infusion pumps include peristaltic pumps, roller pumps, or expulsor pumps, for example. Many of these infusion pumps operate by governing the movement of fluid through delivery tubing by selectively occluding portions of the tubing by depressing a valve or mechanism against the tubing. For example, in some designs the mechanism of a pump selectively engages the tubing against a pressure plate in a peristaltic fashion to force fluid through the tubing.

Various infusion pumps deliver medication from either a disposable medication cassette reservoir or from a disposable administration set having a remote fluid reservoir. Accordingly, these disposables include a pressure plate top surface that is detachably coupled to a bottom surface or chassis of a pump control module. The chassis can be provided with a sensor module with a channel on one surface. A sensor can be provided as part of the channel and detects the presence of air or gas bubbles in tubing. Tubing is provided with and attached to the pressure plate top surface and, when coupled to the pump control module, seats in the channel of the sensor module. The outer wall of the tubing thus makes contact with the channel and the channel sensor can detect the presence of air or gas bubbles in the tubing when fluid is pumped, via the tubing, from the cassette reservoir or the remote fluid reservoir by the control module when the pressure plate is coupled to the control module.

When the pressure plate is properly aligned and connected to the pump control module chassis, a prescribed dose of medication is delivered at a controlled rate to a patient through the tubing connected to the pressure plate. However, if the tubing is improperly seated, blocked, kinked or otherwise impeded by, for example, improper alignment of the pressure plate and pump control module, the patient likely would not receive the prescribed medication, at all or in an intended volume, leading to potentially serious consequences.

Improvements to these types of infusion pump arrangements are desired. For example, ensuring proper alignment of the pressure plate and pump control module is a necessity to the provision of effective infusion pumps. Due to the importance of delivery accuracy and precision in both of the aforementioned cassette-type arrangements and administration-type arrangements, any improvements in these areas would be desirable and a design which can better optimize the interaction and alignment of the pump and pressure plate features would be advantageous.

Therefore, there is a need for improved methods and apparatus for the attachment and alignment between pressure plates and pump control modules in infusion pumps.

SUMMARY

Embodiments relate to methods, systems and devices for ensuring and improving alignment of the pressure plate with the infusion pump control module, thereby providing improved seating and retention of the tubing within a sensor module channel for increased accuracy and effectiveness.

In an embodiment, a medical infusion pump pressure plate alignment system comprises a sensor module, a pressure plate and pressure plate features. The pressure plate has a first end pivotally mounted to the chassis of the control module by way of, for example, hooks which engage corresponding hinge pins in the control module for pivotal retention thereof and a second end selectively engaged with a latching feature of the chassis of the control module optionally by way of, for example, a latch arch. The pressure plate, hooks and optional latch arch can be configured with recesses, projections or other features for receipt of complementary features of the sensor module or of the chassis. Additional alignment features, that can be provided separately or in conjunction with other alignment features, include a retaining component incorporated with the hooks, a guide feature on the outer surface of the pressure plate, and a kickstand feature attached to the rail.

One embodiment is directed to an infusion pump pressure plate alignment system that includes a pressure plate and a sensor module within the chassis of the pump. The pressure plate includes a first end pivotally mounted to the chassis of the control module for pivotal retention and a second end selectively mounted to the chassis of the control module. The pressure plate includes recessed features configured for receipt of projection features of the sensor module.

Another embodiment is directed to an infusion pump pressure plate alignment system that includes a pressure plate and a sensor module within the chassis of the pump. The pressure plate has a first end pivotally mounted to the chassis of the control module for pivotal retention and a second end selectively engaged to the chassis of the control module. The sensor module includes recessed features configured for receipt of projection features of the pressure plate.

Yet another embodiment is directed to an infusion pump pressure plate alignment system that includes a pressure plate and a sensor module within the chassis of the pump. The pressure plate has a first end pivotally mounted to the chassis of the control module for pivotal retention and a second end selectively mounted to chassis of the control module. The pressure plate further has a rail comprised of ramp features configured for mating with ramp features provided on the sensor module.

Another embodiment is directed to an infusion pump pressure plate alignment system that includes a pressure plate and a sensor module within the chassis of the pump. The pressure plate has a first end pivotally mounted to the chassis of the control module for pivotal retention and a second end selectively mounted to the chassis of the control module. The pressure plate further has a rail comprised of male key features configured for mating with female key features provided on the sensor module. In embodiments, the arrangement of the male and female features can be reversed, or some other coupling or mating features can be used.

Another embodiment is directed to an infusion pump pressure plate alignment system that includes a pressure plate and a sensor module within the chassis of the pump. The pressure plate has a first end pivotally mounted to the chassis of the control module for pivotal retention and a second end selectively mounted to the chassis of the control module. The pressure plate further comprises a retaining component on the underside of the hook forming a void contoured to complement the hinge pin between the retaining component and the hook.

A further embodiment is directed to an infusion pump pressure plate alignment system that includes a pressure plate and a sensor module within the chassis of the pump. The pressure plate has a first end pivotally mounted to the chassis of the control module for pivotal retention and a second end selectively mounted to the chassis of the control module. The pressure plate further has a kickstand pivotally attached, via a pin, to the rail. The kickstand is able to rotate forwardly and backwardly about the pin through one range of circular degrees thus ensuring that the pressure plate is mounted correctly to the chassis.

BRIEF DESCRIPTION OF THE DRAWINGS

Subject matter hereof may be more completely understood in consideration of the following detailed description of various example embodiments in connection with the accompanying drawings, in which:

FIG. 11A is a perspective view of alignment features for a pressure plate and complementary alignment features for a sensor module, according to an embodiment.

FIG. 11B is a side wall view of an alternative arrangement of alignment features for a sensor module, according to an embodiment.

FIG. 11C is a perspective view of alignment features for a pressure plate and complementary alignment features for a sensor module, according to an embodiment.

FIG. 12 is a perspective view of alignment features for a pressure plate and complementary alignment features for a sensor module, according to an embodiment.

FIG. 13 is a perspective view of alignment features for a pressure plate and complementary alignment features for a sensor module, according to an embodiment.

FIG. 14A is a perspective view of alignment and retainment features for a pressure plate and infusion pump chassis, according to an embodiment.

FIG. 14B is a perspective view of alignment and retainment features for a pressure plate and infusion pump chassis, according to an embodiment.

Figure 1:
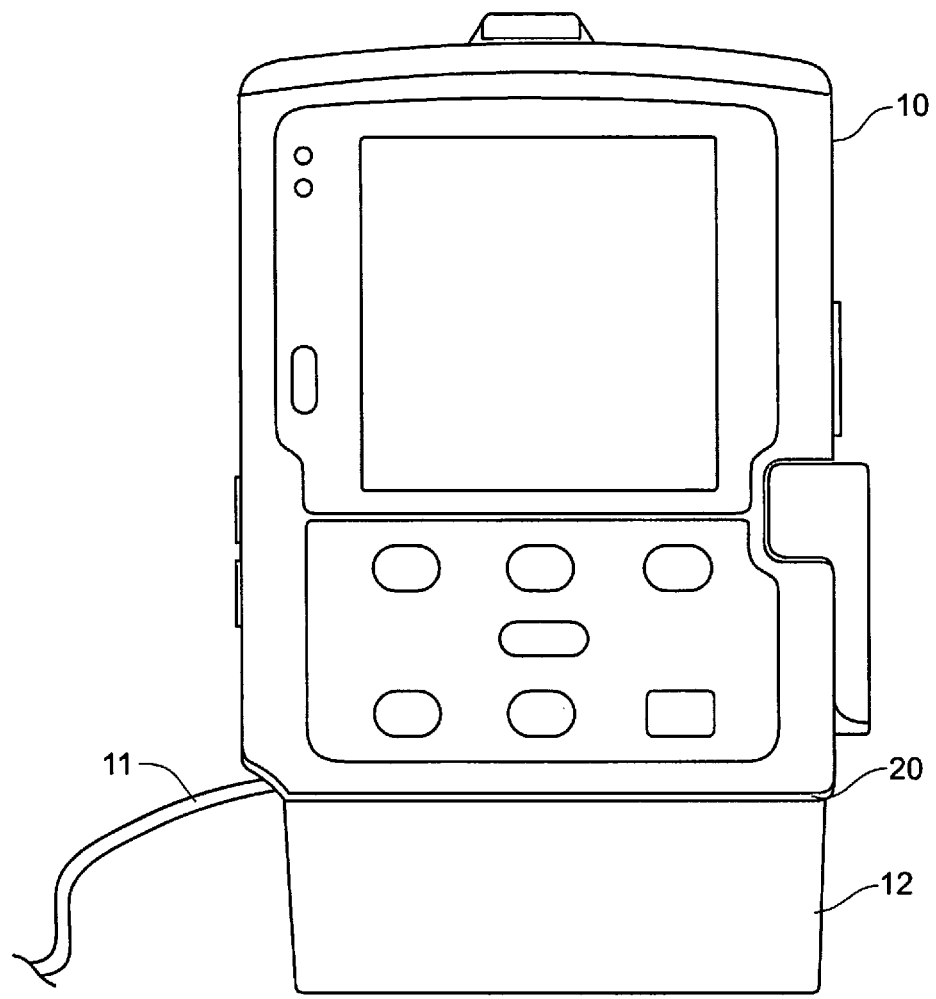
FIG. 1 is a front plan view of an infusion pump with a disposable cassette detachably coupled to the pump according to an embodiment.

While the subject matter hereof is amenable to various modifications and alternative forms, specifics thereof have been shown by way of example in the drawings and will be described in detail. It should be understood, however, that the intention is not to limit the subject matter hereof to the particular embodiments described. On the contrary, the intention is to cover all modifications, equivalents, and alternatives falling within the spirit and scope of the subject matter hereof.

DETAILED DESCRIPTION

Embodiments may be embodied in other specific forms without departing from the essential attributes thereof. The illustrated embodiments should be considered in all respects as illustrative and not restrictive. The following detailed description should be read with reference to the drawings in which similar elements in different drawings are numbered the same.

In various embodiments, devices and methods are disclosed for a pressure plate alignment system. In various embodiments, a pressure plate top surface and a profile of a sensor module are configured with mating surfaces that interface with each other, thus improving or ensuring proper alignment between the disposable component (for example, in the aforementioned cassette-type arrangements and administration-type arrangements) and the pump control module so that the tubing is properly seated in the sensor module.

Components of a pressure plate alignment system, as described by example or otherwise contemplated herein, can be formed or molded from plastic or polymeric materials such as used in fabrication of, for example, disposable medication cassettes. Such materials can include polycarbonate, ABS, polypropylene, polyvinyl chloride, or any other material or blend of materials which would provide desirable properties in construction and use of these components (for example, pressure plate 20, sensor module 30, legs 36, and projections 74, etc.). Still other materials, including metals, alloys, and composites, and combinations of any of these or other materials, also can be used in embodiments.

Figure 2:
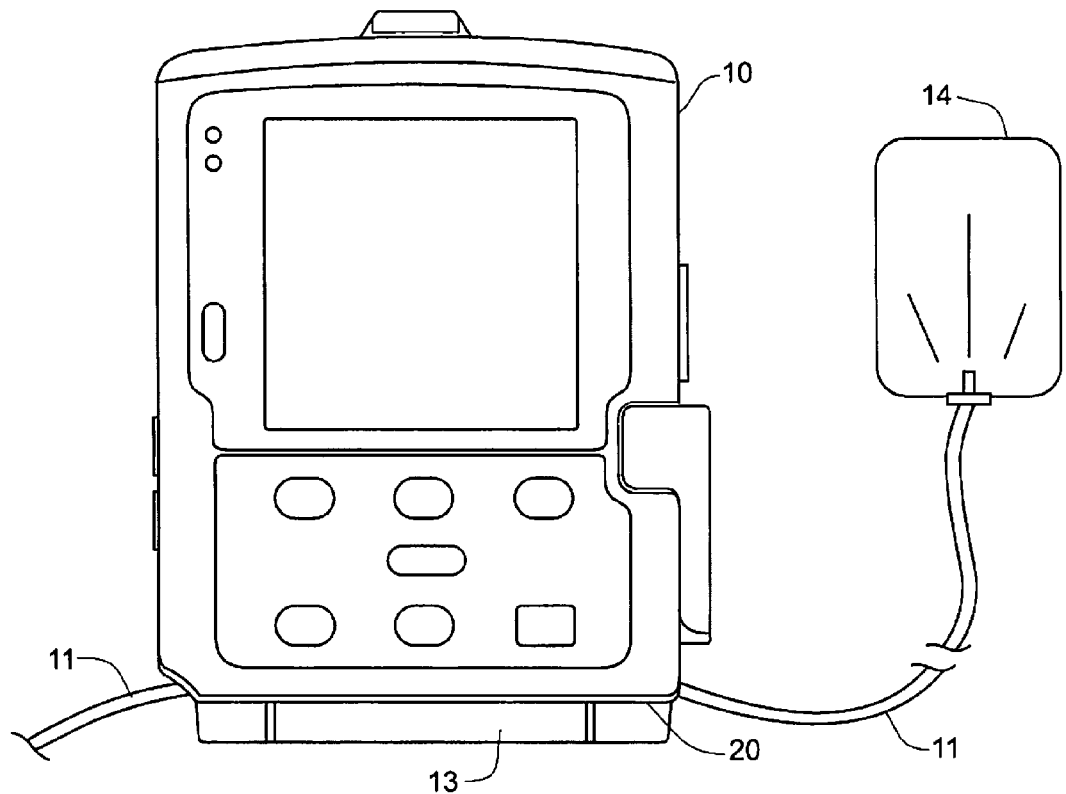
FIG. 2 is a front plan view of an infusion pump with a disposable administration set detachably coupled to the pump according to an embodiment.

FIGS. 1 and 2 depict examples of illustrative arrangements for infusion pumps. These and other types of pressure plate arrangements for disposable cassettes and disposable administration sets for infusion pumps can be further understood from various patents that disclose some common structural and/or operational characteristics. A wide variety of patents disclose some embodiments relating to infusion pump cassettes, pressure plates, and general operation, such as U.S. Pat. Nos. 4,565,542, 5,658,252, 5,772,409, 5,788,671, 5,823,746, 5,928,196, and 5,954,485, for example, which are each hereby incorporated by reference in their entireties.

A pump control module 10, shown in FIG. 1, is operative in effecting the movement of fluid through tubing 11. As illustrated, pump control module 10 is used with a disposable cassette 12 having a fluid reservoir. In FIG. 2, a pump control module 10 is shown as used with a disposable administration set 13. Administration set 13 is coupled to a remote fluid reservoir 14. Common to disposable cassette 12 and disposable administration set 13 is a pressure plate 20, as further depicted in FIG. 3. Tubing is also common to the cassette 12 and the administration set 13 and provides a fluid communication path between the fluid reservoir and the patient via the pressure plate 20. Pressure plate 20 for cassette 12 and administration set 13 is similarly configured with the tubing 11 being disposed on the top surface of the pressure plate 20. In practice, there can be slight differences in the top surface structural configuration for the routing of the tubing 11 but these differences do not affect embodiments as discussed herein.

Figure 3:
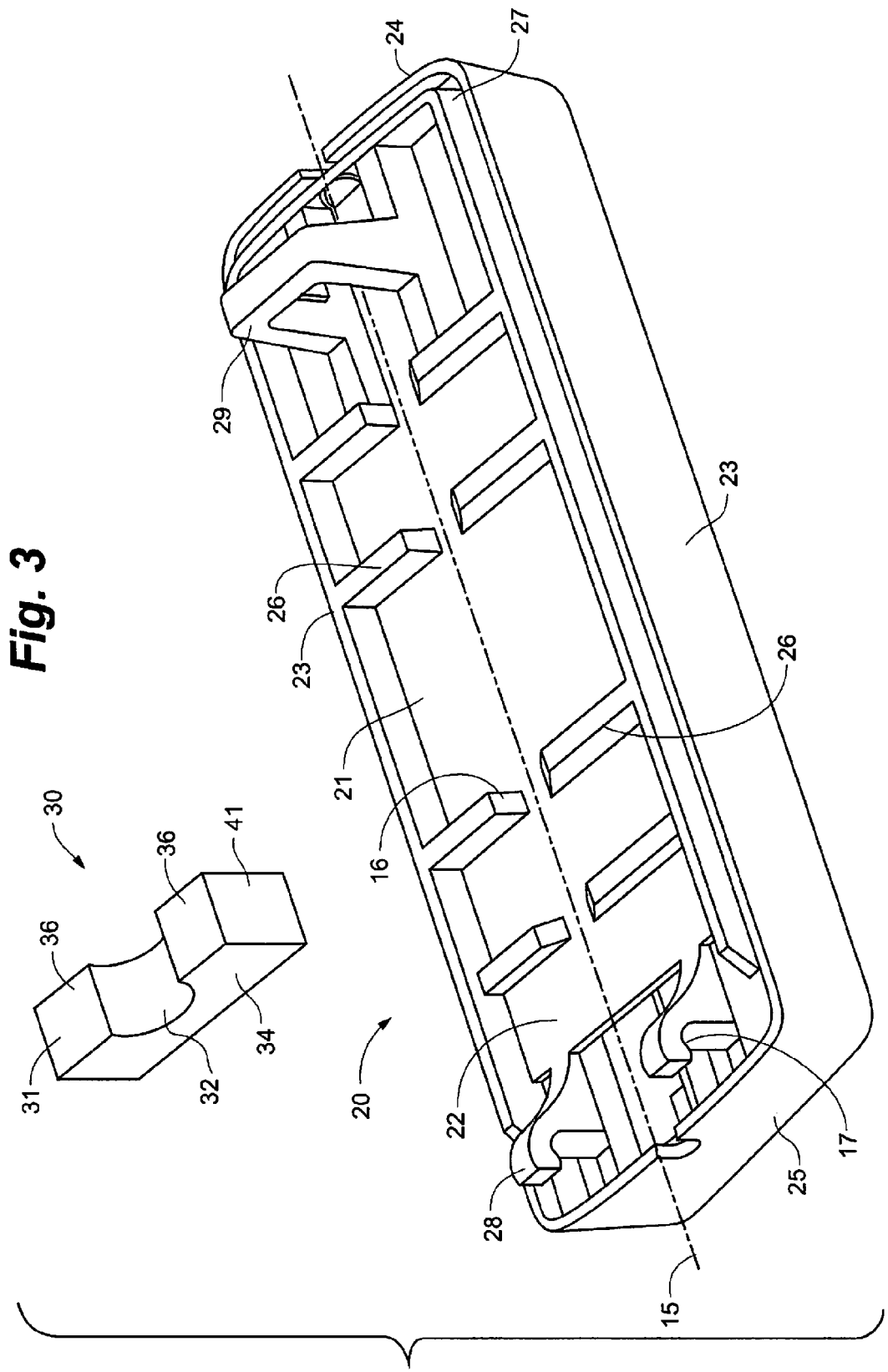
FIG. 3 is a perspective view of a pressure plate and sensor module, for use in an infusion pump, having guides and alignment features for tubing according to an embodiment.

FIG. 3 depicts a typical pressure plate 20 and a sensor module 30. Pressure plate 20 includes a top surface 21 and a bottom surface (not shown), two side walls 23, an upstream wall 24 and a downstream wall 25. Pressure plate 20 includes a plurality of guides 26 positioned generally perpendicularly to side walls 23 on top surface 21 of pressure plate 20. Guides 26 are generally provided in pairs, with an end 16 of each guide 26 in a pair being spaced on either side of a longitudinal axis 15. Guides 26 align and maintain tubing 11, as shown in FIGS. 1 and 2, longitudinally in place on pressure plate 20. Each guide 26 can have an end 16 with a sloped surface contoured to contact tubing 11. In other embodiments, guide ends 16 can be planar and orthogonal to top surface 21. In another embodiment, guide ends 16 can be provided with a concave configuration that matches the contours of tubing 11. Other shapes and configurations of guide 16 can be used in other embodiments, Also, it is to be appreciated and understood that as described by example or otherwise contemplated herein, referenced "tubing" can actually comprise two tube materials of different diameters to optimize functioning of an infusion pump, with the two tube materials being joined together by any suitable fluid-tight means. Thus, for example, a portion of tubing 11 that would extend across plate 20 along longitudinal axis 15 and between guides 26 (as shown in FIG. 3) can be of a diameter that is larger than another portion of tubing 11 that extends outwardly from plate 20 (to the left and/or to the right in FIG. 2).

Figure 4:
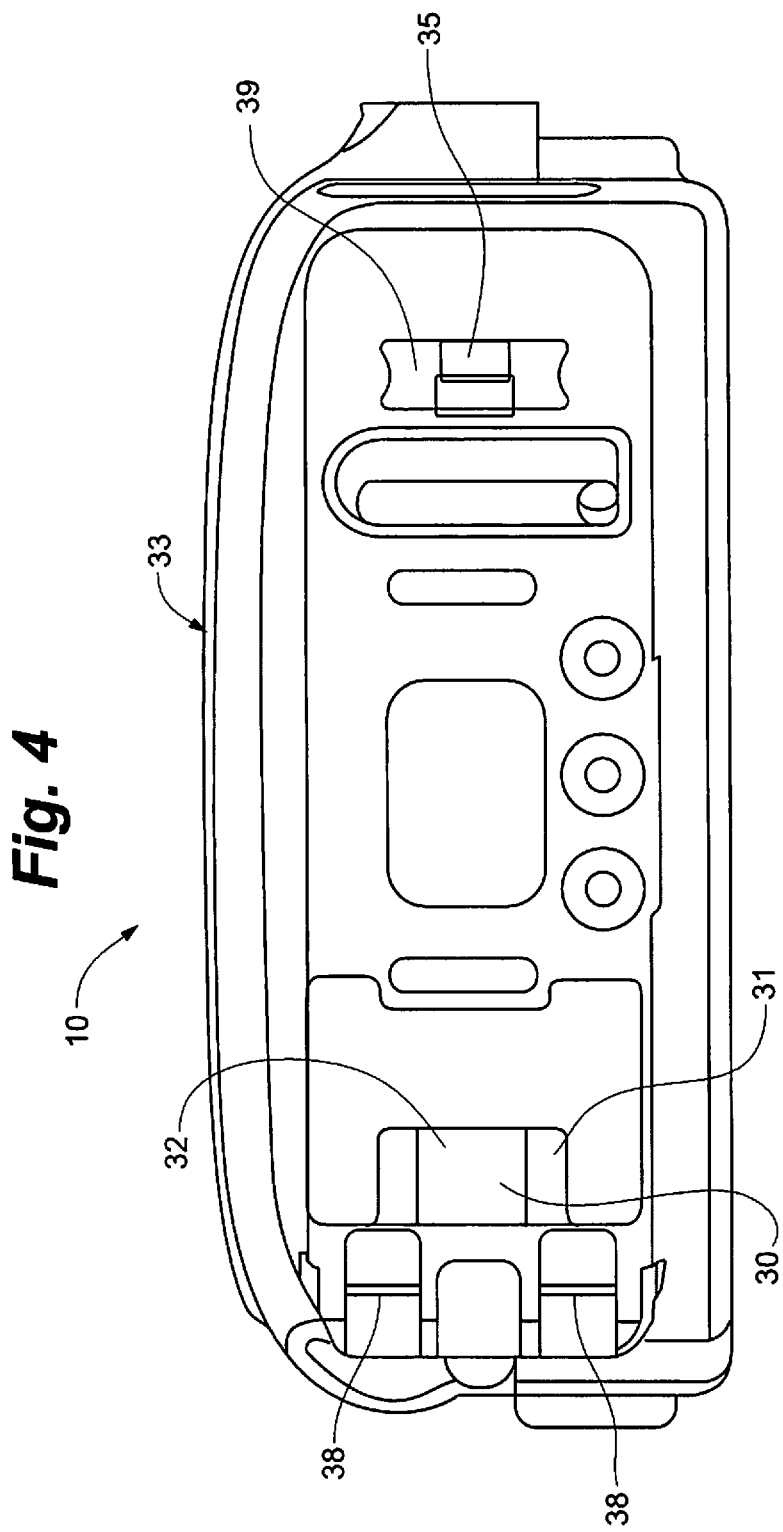
FIG. 4 is a bottom view of an infusion pump chassis detailing attachment features and the sensor module location according to an embodiment.

Pressure plate 20 also includes a rail 27 which substantially surrounds pressure plate 20 and is adjacent to chassis 33 (as shown in FIG. 4) of the pump control module 10. Pressure plate 20 includes hooks 28 that extend from top surface 21 adjacent to a downstream wall 25 end, and a latch arch 29 extending from top surface 21 adjacent to an upstream wall 24 end. Hooks 28 are formed so that each has an underside 17 with a slight concave curve. Guide 26 pairs are spaced from each other generally perpendicularly to rail 27 and thus visibly define sections in top surface 21 of pressure plate 20. One such section closest to downstream wall 25 and adjacent hooks 28 is hereinafter referred to as a pressure plate floor 22.

Sensor module 30, shown in FIG. 3, is provided as a component of the pump control module 10 in embodiments. Sensor module 30 is generally rectangular in shape, having a planar surface 31 that has a channel 32 formed therewithin and thus visibly defining legs 36. As such, the sensor module 30 partially defines the channel 32. Orthogonal to the surface 31 are side walls 34. Perpendicular to side walls 34 are end walls 41. Channel 32 complements the contours of tubing 11 and can house one or more sensor elements (not illustrated) for sensing properties including, but not limited to, fluid, gas, or air within tubing 11. Thus, in embodiments, sensor module 30 can comprise an air detector sensor module. Attachment of pressure plate 20 to chassis 33 of the pump control module 10 results in sensor module planar surface 31 being aligned with the planar surface of pressure plate floor 22 and tubing 11 being aligned within channel 32. One advantage of embodiments is receiving the correct, for example, fluid/air readings due to the correct positioning of tubing 11 within sensor module channel 32 resulting from the proper alignment of sensor module 30 and tubing 11.

Figure 5:
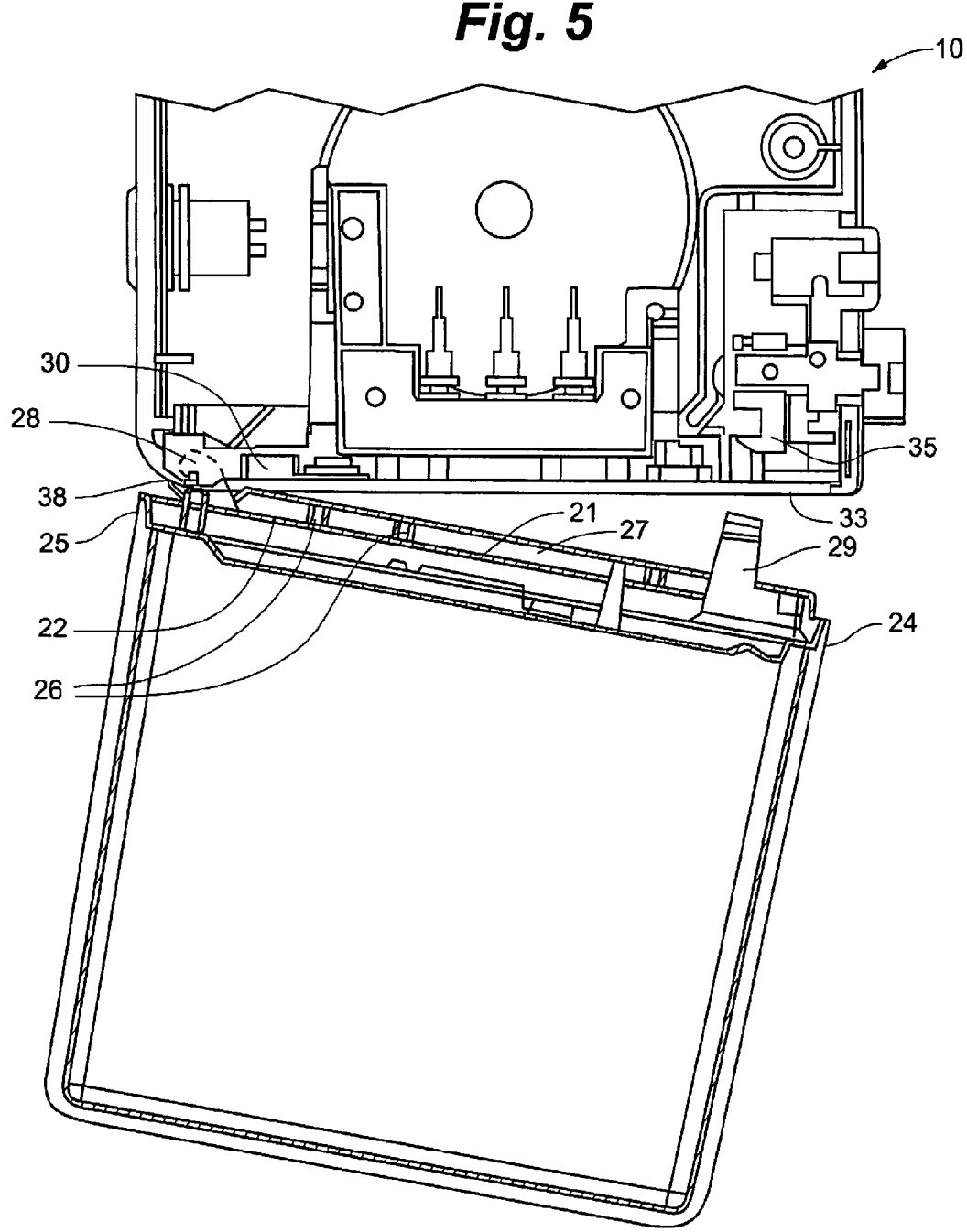
FIG. 5 is a cut away view of the an infusion pump with a disposable cassette showing the pressure plate hooks rotatably connected to the hinge pins according to an embodiment.

The bottom of pump control module 10, comprising chassis 33, is depicted in FIG. 4. Chassis 33 includes a sensor module 30, hinge pins 38, and a recess 39 including a latch 35 in an embodiment. Sensor module 30 is provided in chassis 33 so that planar surface 31 and channel 32 are outwardly facing. The outer edge of chassis 33 fittingly engages pressure plate 20. In particular, as shown in FIG. 5, attachment of pressure plate 20 to chassis 33 comprises a hinge and latch type arrangement in embodiments. Attachment involves first aligning the underside 17 of hooks 28 with hinge pins 38 so that underside 17 of hooks 28 are disposed on and rotatingly engage hinge pins 38. Thus, upstream wall 24 end of pressure plate 20 is unattached and pressure plate 20, via hooks 28, can be freely rotated on hinge pins 38. To complete the attachment process, upstream wall 24 end is urged towards chassis 33 and latch arch 29 is received within recess 39. Recess 39 includes a latch 35 which selectively engages latch arch 29 to lock pressure plate 20 to pump control module 10. When pressure plate 20 is locked to pump control module 10, tubing 11 is positioned in sensor module channel 32 and, is also located longitudinally between guides 26. Positioned as such, tubing 11 is thus generally parallel to side walls 23 and substantially follows longitudinal axis 15 between upstream wall 24 and downstream wall 25. When pressure plate 20 and chassis 33 are correctly aligned and attached, sensor module surface 31 is facing pressure plate floor 22 so that sensor module surface 31 is parallel to and aligned with floor 22. However, it is possible to misalign pressure plate 20 and chassis 33 and would therefore be understood to one skilled in the art that additional alignment features could help to negate any propensity for misalignment.

Disclosed below are other embodiments of alignment features for positively aligning pressure plate 20 and chassis 33. The alignment features provide surfaces or components on pressure plate 20 that positively mate with complementary surfaces or features on sensor module 30 or chassis 33.

Figure 6:
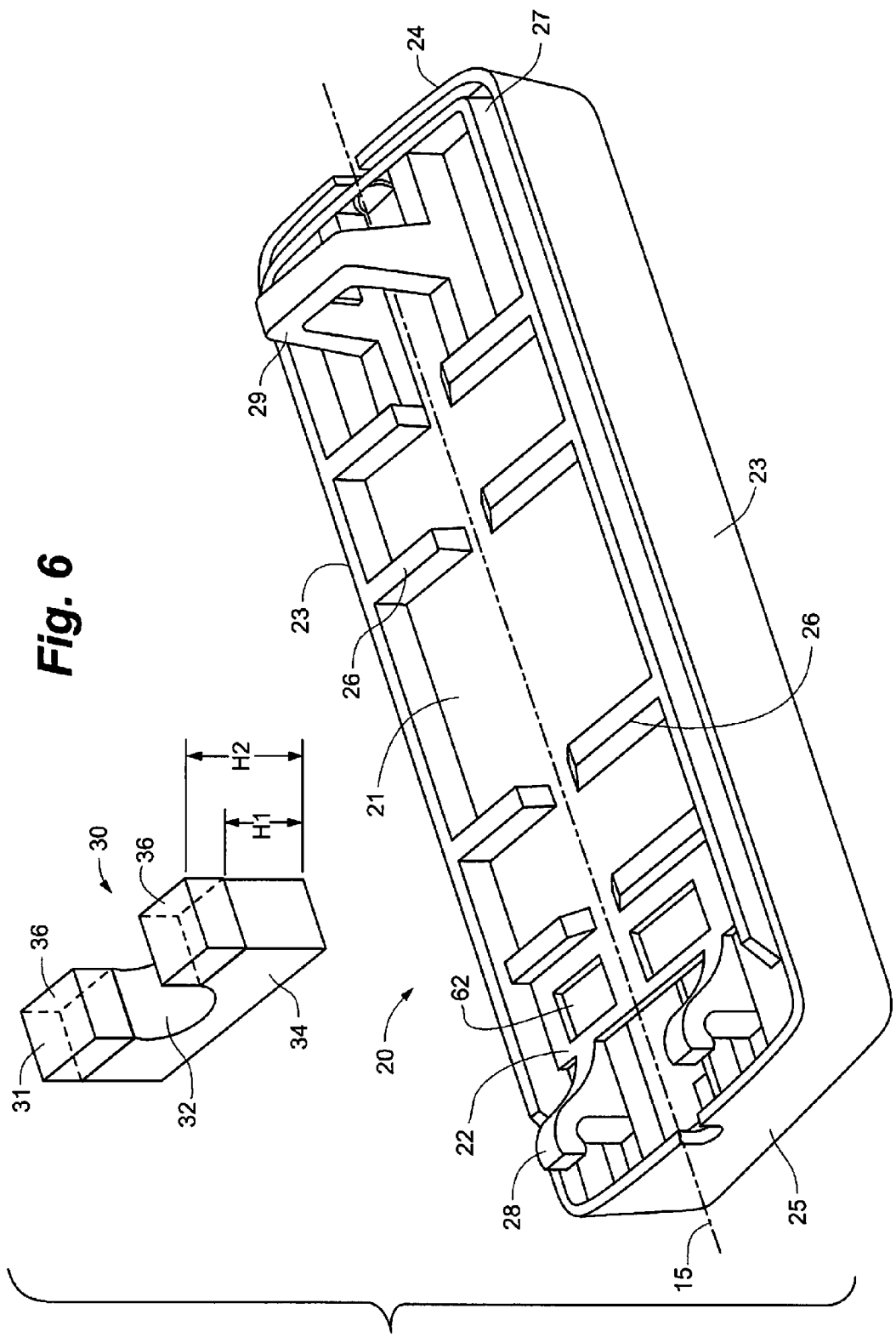
FIG. 6 is a perspective view of alignment features for a pressure plate and complementary alignment features for a sensor module, according to an embodiment.

FIG. 6 depicts one embodiment of an alignment feature. Sensor module 30 comprises legs 36 having an increased height where the altered height H2 of sensor module 30 is greater than the standard height HI. Pressure plate 20 is provided with two recesses 62 disposed on pressure plate floor 22. Recesses 62 are located on each side of and substantially equidistant from longitudinal axis 15. The outer dimensions of recesses 62 are such that they fittingly receive sensor module legs 36. It is also contemplated that through-holes can be provided on floor 22 in embodiments. In an embodiment, when attaching pressure plate 20 to chassis 33, sensor module legs 36 fittingly engage with platform recesses 62 resulting in proper alignment of pressure plate 20 and chassis 33. It is contemplated that in embodiments recesses 62, legs 36, or both can be chamfered.

One advantage of aligning pressure plate 20 and chassis 33, for this and other embodiments, is that tubing 11 is more likely to be properly seated in sensor module 30.

Another advantage, for this and other embodiments, is that attachment of pressure plate 20 to chassis 33 is tangibly inhibited if the alignment is not correct.

Figure 7:
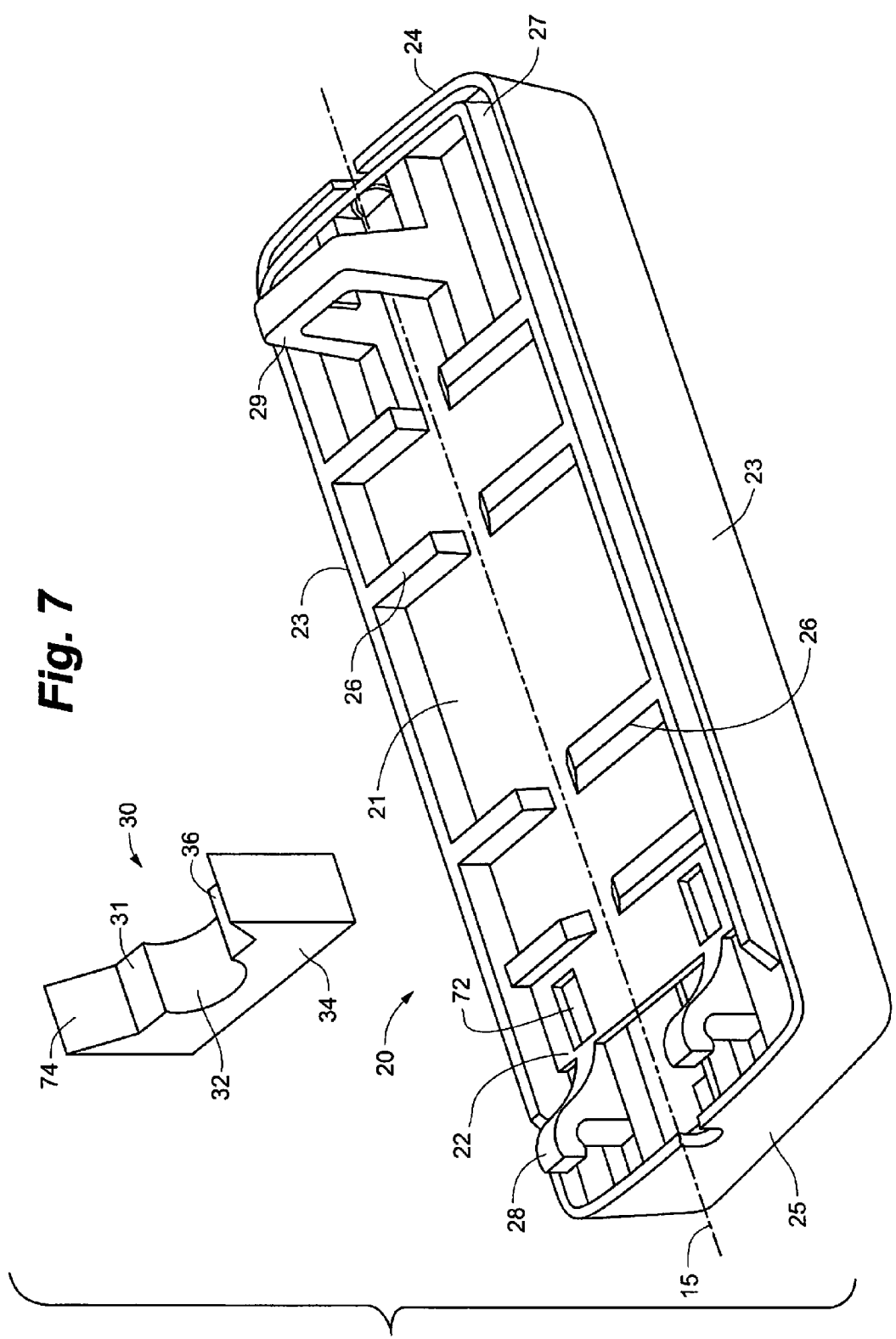
FIG. 7 is a perspective view of alignment features for a pressure plate and complementary alignment features for a sensor module, according to an embodiment.

FIG. 7 illustrates another embodiment of an alignment feature. Sensor module 30 comprises tapered projections 74 extending from planar surface 31. Pressure plate 20 is provided with slot-type recesses 72 disposed on pressure plate floor 22. Recesses 72 are located on each side of and substantially equidistant from longitudinal axis 15. The outer dimensions of recesses 72 are such that they fittingly receive projections 74. It is also contemplated that through-holes can be provided on floor 22. While projections 74 and recesses 72 are depicted in FIG. 7 as being generally triangular in shape, projections 74 and complementary recesses 72 can be of any shape, i.e., square, rectangular, pyramidal, cylindrical, half-spherical, etc Additionally, projections 74, while shown to be at the outer edges of legs 36, can be positioned at any location upon surface 31 with a matching recess 72 location provided on floor 22. in embodiments, when attaching pressure plate 20 and chassis 33, the projections 74 fittingly engage with platform recesses 72 resulting in proper alignment of pressure plate 20 and chassis 33. It is contemplated that in embodiments recesses 72, projections 74, or both can be chamfered.

Figure 8:
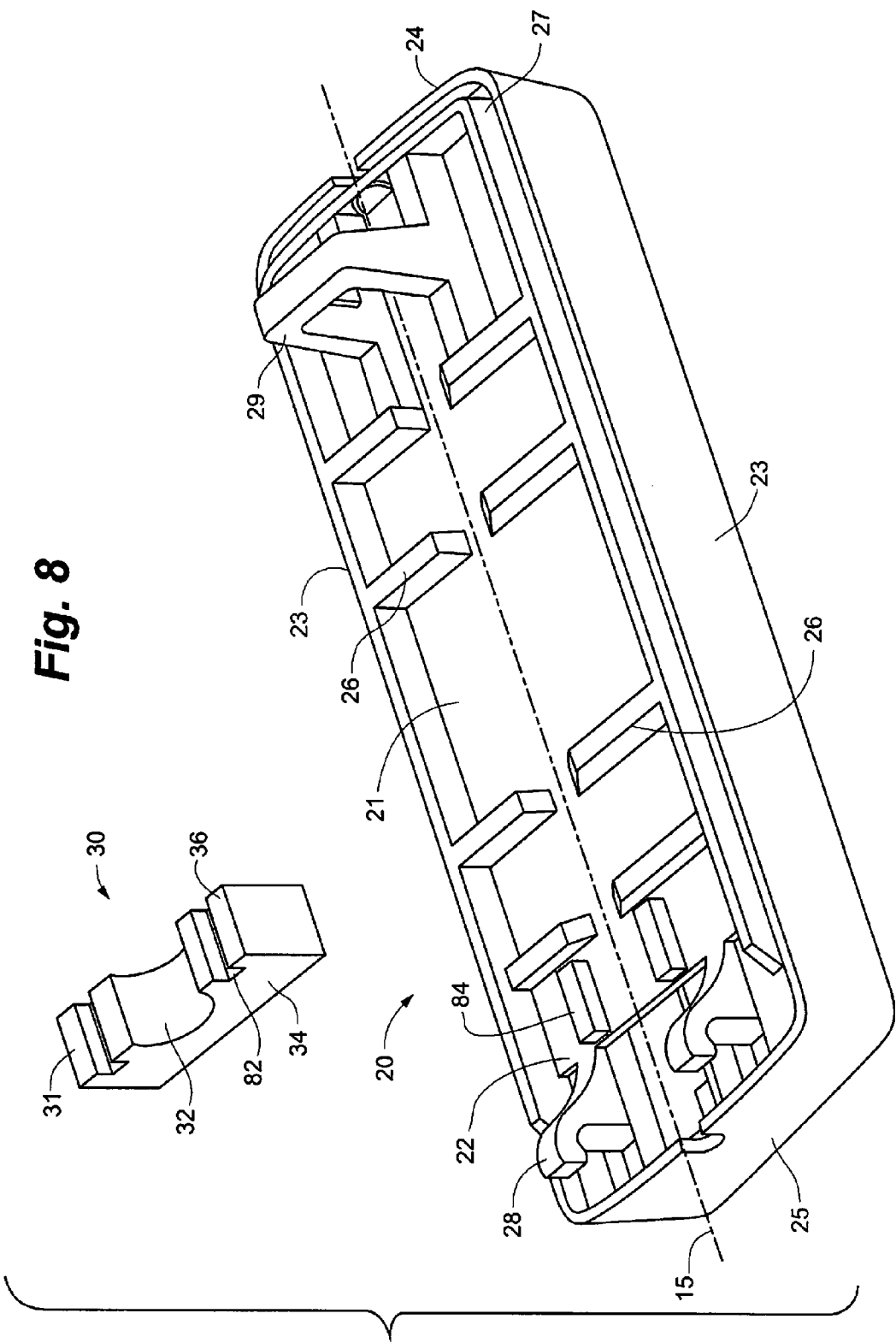
FIG. 8 is a perspective view of alignment features for a pressure plate and complementary alignment features for a sensor module, according to an embodiment.

FIG. 8 illustrates another embodiment of an alignment feature, In this embodiment, pressure plate 20 is provided with projections 84 disposed on pressure plate floor 22 and sensor module 30 is provided with recesses 82 on a portion of surface 31. The projections 84 are located on each side of longitudinal axis 15. The outer dimensions of recesses 82 are such that they fittingly receive projections 84. While projections 84 and recesses 82 are depicted as being substantially rectangular in shape, projections 84 and complementary recesses 82 can be of any shape, i.e., square, triangular, pyramidal, cylindrical, half-spherical, etc. Additionally, recesses 82, while shown to be near the midpoint of legs 36, can be positioned at any location upon surface 31 with a matching projection 84 location provided on floor 22. In embodiments, when attaching pressure plate 20 and chassis 33, projections 84 fittingly engage with platform recesses 82 resulting in proper alignment of pressure plate 20 and chassis 33. It is contemplated that in certain embodiments recesses 82, projections 84, or both can be chamfered.

Figure 9:
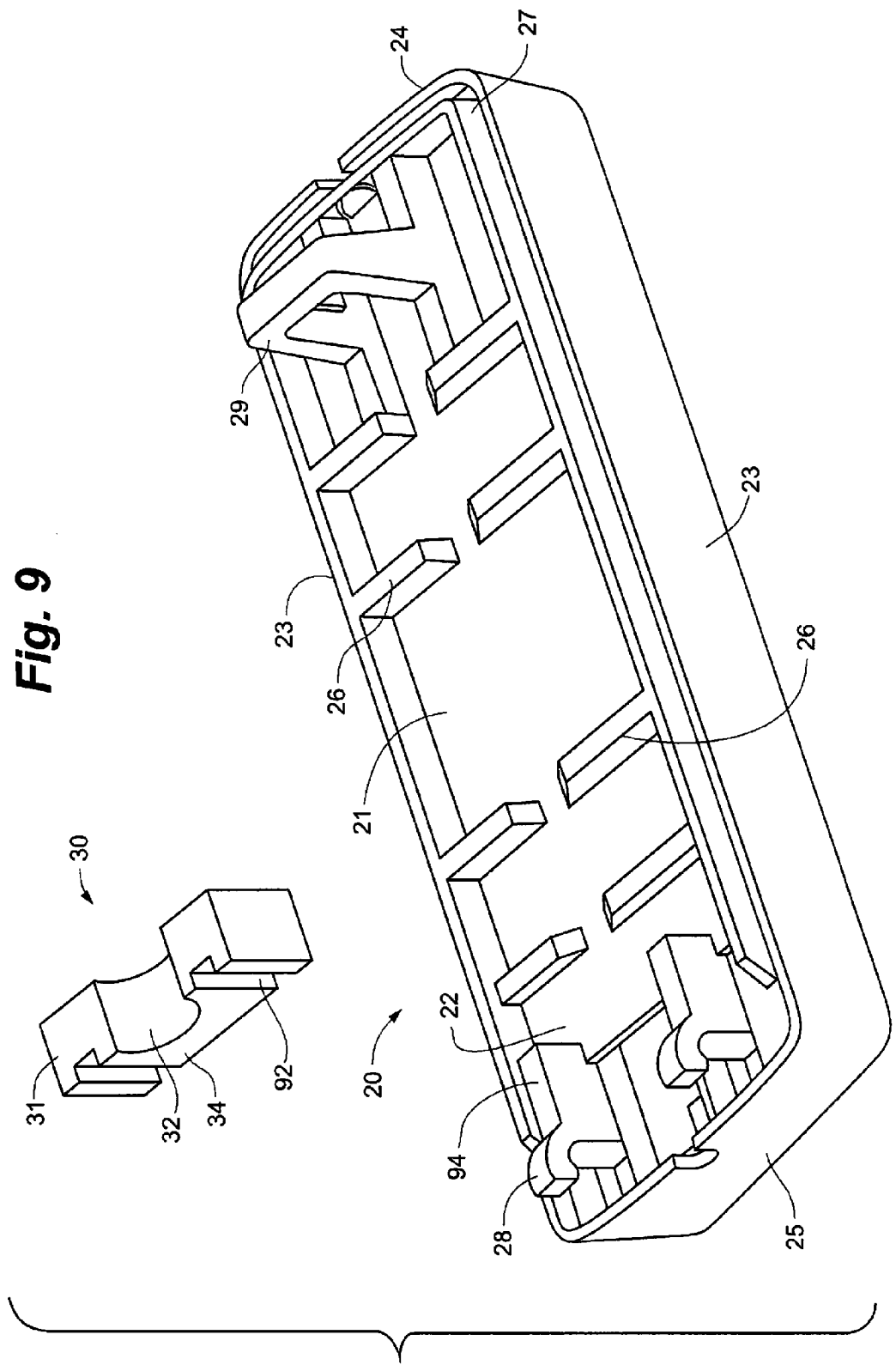
FIG. 9 is a perspective view of alignment features for a pressure plate and complementary alignment features for a sensor module, according to an embodiment.

FIG. 9 depicts another embodiment of an alignment feature, In this embodiment, hooks 28 are provided with projections 94 extending over a portion of pressure plate floor 22. Sensor module 30 side wall 34 is provided with recesses 92 complementing the shape of hook projections 94. While projections 94 and recesses 92 are depicted as being rectangular in shape, projections 94 and complementary recesses 92 can be of any shape, i.e., square, triangular, cylindrical, etc. in an embodiment, when attaching pressure plate 20 and chassis 33, projections 94 fittingly engage with side wall recesses 92 resulting in proper alignment of pressure plate 20 and chassis 33. It is contemplated that in embodiments recesses 92, projections 94, or both can be chamfered.

Figure 10:
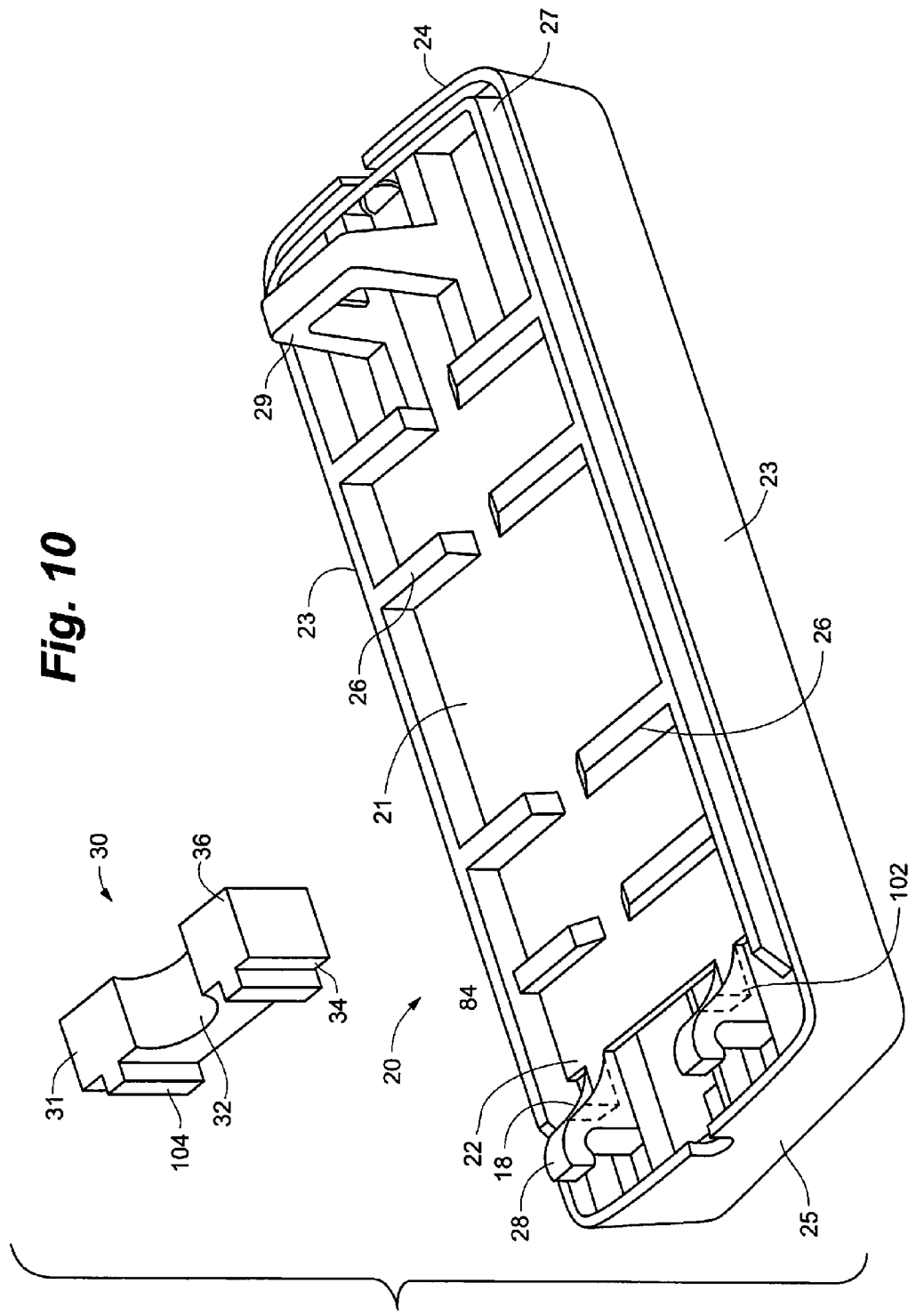
FIG. 10 is a perspective view of alignment features for a pressure plate and complementary alignment features for a sensor module, according to an embodiment.

FIG. 10 depicts another embodiment of an alignment feature having recesses or slots 102 provided on the rear side 18 of hooks 28. Sensor module 30 is provided with projections 104 on side wall 34. Projections 104 complement the shape of recesses 102 provided in hooks 2.8. While projections 104 and recesses 102 are depicted as being rectangular in shape, projections 104 and complementary recesses 102 can be of any shape, i.e., square, triangular, cylindrical, etc. In an embodiment, when attaching pressure plate 20 and chassis 33, recesses 102 fittingly engage with side wall projections 104 providing guidance and alignment of pressure plate 20 and chassis 33. It is contemplated that in embodiments recesses 102, projections 104, or both can be chamfered.

FIG. 11A depicts another embodiment of an alignment feature for pressure plate 20 and chassis 33. In this embodiment, channel feature 110 is provided on pressure plate floor 22. Numerous alternate embodiments are contemplated in relation to providing a channel feature 110 on floor 22. Each of the following channel feature 110 embodiments would entail sensor module 30 having complementary recesses or ledges. Additionally, channel feature 110 embodiments each have projections 114, where projections 114 are generally mirror images of each other and are located on each side of longitudinal axis 15. Projections 114 can be substantially rectangular. It is also contemplated that surface 116 of each projection 114 can be concave or angled so that surfaces 116 substantially complement the contours of tubing 11.

Channel feature 110, of FIG. 11A is comprised of two projections 114, each extending longitudinally on pressure plate floor 22 and parallel to each other. Channel feature 110 aligns tubing 11 and also correspondingly mates with a ledge 112 provided on sensor module 30. Ledges 112 are provided on either side of sensor module channel 32. In one embodiment, ledges 112 intersect with channel 32. In another embodiment, as shown in FIG. 11B, ledges 112 are separated from channel 32 by a portion 118 of leg 36. Accordingly, channel feature 110 located on pressure plate floor 22 may be spatially adjusted in relation to longitudinal axis 15 to compensate for the portion 118 of the leg to be sandwiched between tubing 11 and channel feature 110. The sensor module 30 is provided with ledges 112 formed to complement channel feature 110 so that ledges 112 fittingly engage with channel feature 110 upon attachment of pressure plate 20 to chassis 33. It is contemplated that in embodiments ledges 112, channel features 110, or both can be chamfered.

Another embodiment of a channel feature 110 and corresponding sensor module 30 is shown in FIG. 11C. The embodiment depicts a separated channel feature 110, each side of channel feature 110 having two projections 114. Channel feature 110 is formed with a gap to provide an opening for sensor module 30 to sense fluid, gas, or air as aforementioned in tubing 11. The complementary sensor module 30 is provided with recesses 113 that match the shape and location of separated channel feature projections 114. An alternate embodiment provides for projections 114 to be spaced such that complementary sensor module recesses 113 intersect with sensor module channel 32, in yet another embodiment (not shown), channel feature 110 of FIG. 11C is provided with a single projection 114 on each side of longitudinal axis 15 and a complementary sensor module 30 is provided in the chassis 33. The single projections 114 can be located anywhere on the pressure plate floor 22, adjacent guide 26, nearer downstream wall 25, or centered, between guide 26 and downstream wall 25. The complementary sensor module 30 is provided with recesses 113 that match the shape and location of the single projection 114 on each side of longitudinal axis 15.

FIG. 12 illustrates an embodiment of an alignment feature provided to align pressure plate 20 and chassis 33. Complementary ramps 122, 124 are provided, respectively, on rails 27 opposite of each other and on both end walls 41 of sensor module 30. Rails 27 are formed having ramps 122 that extend over a portion of pressure plate floor 22. Sensor module 30 end walls 41 are provided with ramps 124 that complement rail ramps 122. In an embodiment, attachment of pressure plate 20 to chassis 33, results in ramps it 22, it 24 fittingly engaging with each other to properly align pressure plate 20 and chassis 33. It is contemplated that in embodiments one or both ramps 122, it 24 can be chamfered.

FIG. 13 illustrates another embodiment of an alignment feature provided to align pressure plate 20 and chassis 33. Male keys 132 are provided on rails 27 opposite of each other and extend over a portion of pressure plate floor 22, while complementary female sockets 134 are provided at interior end walls 41 of sensor module 30. The shapes of male keys 132 and female sockets 134 are not limited so long as an interlocking connection can be made. In an embodiment, attaching pressure plate 20 and chassis 33, male keys 132 and female sockets 134 fittingly engage with each other resulting in alignment of pressure plate 20 and chassis 33. It is contemplated that in embodiments keys 132, sockets 134 or both can be chamfered.

Depicted in FIG. 14A is an embodiment of an alignment and attachment feature comprised of a retaining component 140 formed as part of the hook 28 structure. Retaining component 140 extends from the top surface of pressure plate 20 toward underside 17 of hook 28. Hinge pin 38 contacts top surface 142 of retaining component 140 with top surface 142 being configured to conform to the contour of hinge pin 38. As depicted in FIG. 14B, hinge pin 38 is inserted into the void between underside 17 of hook 28 and retaining component 140 by forcing hinge pin 38 into the area between hook point 144 and retaining component point 146. A distance d between points 144, 146 is slightly less than a diameter D of hinge pin 38. Thus, when inserted into the void, hinge pin 38 is frictionally retained in the void between underside 17 of hook 28 and retaining component 140 thereby prevents slippage of hook 28 from hinge pin 38 and thus assists pressure plate 20 in retaining alignment to chassis 33.

Figure 15:
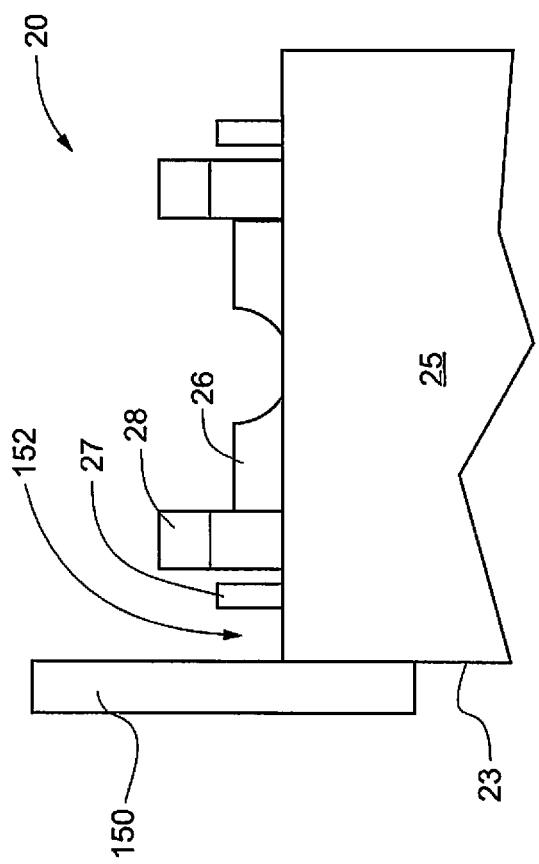
FIG. 15 is a perspective view of alignment features for a pressure plate and infusion pump chassis, according to an embodiment.

Depicted in FIG. 15 is an embodiment of an alignment feature comprising a guiding component 150 formed as part of the pressure plate structure. Guiding component 150 is provided to extend from side wall 23 of pressure plate 20 and terminate at a point higher than the top surface of rail 27. When attaching pressure plate 20 to chassis 33, guiding component 150 contactingly slides along the outer back area of pump module 10 so that chassis 33 fits snugly within void 152 between guiding component 150 and rail 27, thereby aligning pressure plate 20 with chassis 33.

Figure 16:
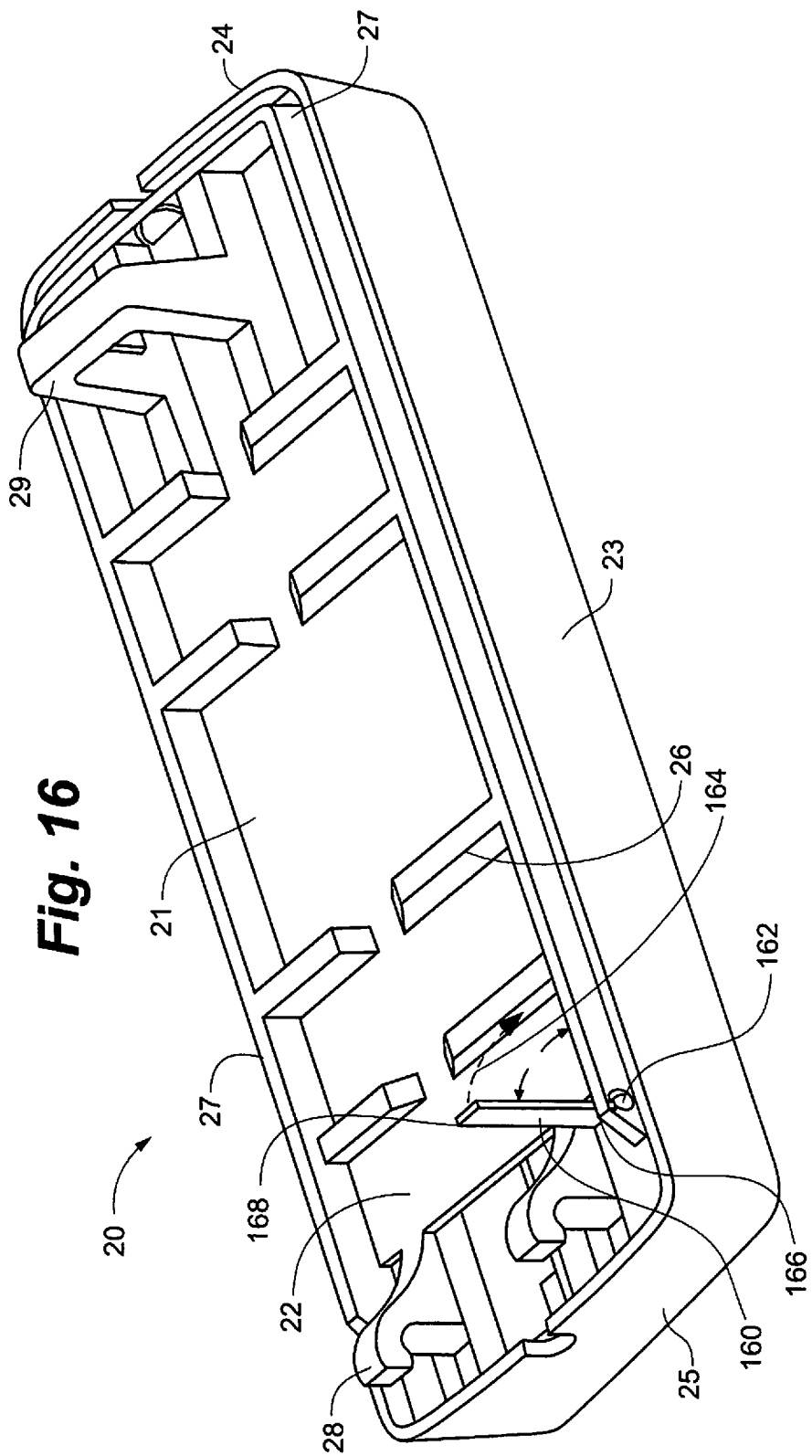
FIG. 16 is a perspective view of attachment features for a pressure plate, according to an embodiment.

FIG. 16 depicts an embodiment of an attachment feature comprised of a kickstand 160 to prevent attachment of pressure plate 20 to chassis 33 when hooks 28 are not disposed on or are improperly disposed on hinge pins 38. Kickstand 160 is pivotally attached at its distal end 166 to rail 27 by a pin 162. Kickstand 160 rotates forwardly and backwardly about pin 162 as indicated by arrow 164 through one range of circular degrees. Kickstand 160 can rotate so that it lies substantially parallel to top surface 21 of pressure plate 20. Upon attachment of hooks 28 of pressure plate 20 to hinge pins 38 of chassis 33, proximal end 168 of kickstand 160 makes contact with the bottom of chassis 33. As upstream wall 24 end is urged towards chassis 33, kickstand 160 will rotate in the direction 164 shown, due to the angle θ of the connection between kickstand 160 and rail 27, and lie substantially parallel to top surface 21 of pressure plate 20, thereby completing the attachment process, where latch 35 (in the chassis) engages latch arch 29 to lock pressure plate 20 to pump control module 10.

Alternatively, when pressure plate hooks 28 are not properly attached or not attached to hinge pins 38 on chassis 33, kickstand 160 will not rotate in direction 164 shown due to angle θ of the connection between kickstand 160 and rail 27, thereby tangibly inhibiting incorrect alignment and attachment of chassis 33 to pressure plate 20.

Any particular relative arrangements discussed and depicted herein can vary in embodiments in which other configurations are implemented. For example, in an embodiment in which tubing 11 follows an at least partially curvilinear or radial path, other components may be adjusted, adapted or arranged accordingly. Moreover, disposables other than tubing 11 can be used with the medical infusion pump in embodiments, with components and features of the alignment system adapted to suit the disposable and the pump and still provide proper seating, alignment or some other configuration for proper operation.

It should also be appreciated that the exemplary embodiment or exemplary embodiments are only examples, and are not intended to limit the scope, applicability, or configuration of the subject matter hereof in any way. Rather, the foregoing detailed description will provide those skilled in the art with an enabling disclosure for implementing the exemplary embodiment or exemplary embodiments. It should be understood that various changes can be made in the function and arrangement of elements without departing from the scope of the subject matter hereof as set forth in the appended claims and the legal equivalents thereof.

The embodiments above are intended to be illustrative and not limiting. Additional embodiments are within the claims. Although the present subject matter has been described with reference to particular embodiments, workers skilled in the art will recognize that changes may be made in form and detail without departing from the spirit and scope of the subject matter hereof.

Various modifications to the subject matter hereof may be apparent to one of skill in the art upon reading this disclosure. For example, persons of ordinary skill in the relevant art will recognize that the various features described for the different embodiments of the subject matter can be suitably combined, un-combined, and re-combined with other features, alone, or in different combinations, within the spirit of the subject matter hereof. Accordingly, the embodiments are not mutually exclusive combinations of features; rather, the invention can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim. Likewise, the various features described above should all be regarded as example embodiments, rather than limitations to the scope or spirit of the subject matter hereof. Therefore, the above is not contemplated to limit the scope of the present subject matter hereof.

Any incorporation by reference of documents above is limited such that no subject matter is incorporated that is contrary to the explicit disclosure herein. Any incorporation by reference of documents above is further limited such that any definitions provided in the documents are not incorporated by reference herein unless expressly included herein.

For purposes of interpreting the claims for the present subject matter, it is expressly intended that the provisions of Section 112, sixth paragraph of 35 U.S.C. are not to be invoked unless the specific terms "means for" or "step for" are recited in a claim.

The invention claimed is:

1. A medical infusion pump pressure plate alignment system, comprising:
   a control module including a chassis, the chassis having a first end and a second end;
   at least one hinge pin disposed on and adjacent to the first end of the chassis;
   a sensor module on the chassis, the sensor module including a planar top surface, with the planar top surface including a sensor channel defining at least two legs; and
   a pressure plate having at least one hook and a floor adjacent the at least one hook, wherein the at least one hook is configured to pivotally mount to the at least one hinge pin so that the at least two legs of the planar top surface of the sensor module aligns with and contactingly engages the floor, wherein the at least one hook comprises a projection and a side wall of the sensor module comprises at least one recess, wherein the projection of the hook is configured to fittingly engage with the recess.

2. The pressure plate alignment system of claim 1, wherein the floor further comprises at least two recesses, and wherein the at least two legs are configured to fittingly engage with the at least two recesses, respectively.

3. The pressure plate alignment system of claim 1, wherein:
   the floor comprises at least one recess; and
   the planar top surface comprises at least one projection, wherein the at least one projection is configured to fittingly engage with the at least one recess.

4. The pressure plate alignment system of claim 1, wherein:
   the floor comprises at least one projection; and
   the planar top surface comprises at least one recess wherein the at least one recess is configured to fittingly engage with the at least one projection.

5. The pressure plate alignment system of claim 1, wherein the pressure plate comprises a first side wall, at least one guide component disposed on the first side wall, the guide component extending beyond the first side wall.

6. The pressure plate alignment system of claim 1, wherein:
   the pressure plate includes at least one kickstand; and
   a rail substantially surrounds the pressure plate, wherein the at least one kickstand is configured (i) to pivotally attach to the rail and (ii) to have a mounting angle allowing forward and backward movement thereof.

7. A medical infusion pump pressure plate alignment system, comprising:
   a control module including a chassis, the chassis having a first end and a second end;
   at least one hinge pin disposed on and adjacent to the first end of the chassis;
   a sensor module on the chassis, the sensor module including a planar top surface, with the planar top surface including a sensor channel defining at least two legs; and
   a pressure plate having at least one hook and a floor adjacent the at least one hook, wherein the at least one hook is configured to pivotally mount to the at least one hinge pin so that the at least two legs of the planar top surface of the sensor module aligns with and contactingly engages the floor wherein:
   the pressure plate includes a rail surrounding the pressure plate;
   the rail includes an inner wall, with the inner wall including at least one ramp type projection; and
   the sensor module includes an end wall, with the end wall including at least one ramp type projection configured to fittingly engage with the ramp type projection of the rail.

8. The pressure plate alignment system of claim 7, wherein the floor further comprises at least two recesses, and wherein the at least two legs are configured to fittingly engage with the at least two recesses, respectively.

* * * * *